United States Patent [19]

Richardson et al.

[11] Patent Number: 4,459,854
[45] Date of Patent: Jul. 17, 1984

[54] ULTRASONIC TRANSDUCER COUPLING MEMBER

[75] Inventors: Paul C. A. Richardson, Guildford; Andrew L. Stevens, London, both of England

[73] Assignee: National Research Development Corporation, London, England

[21] Appl. No.: 399,954

[22] Filed: Jul. 19, 1982

[30] Foreign Application Priority Data

Jul. 24, 1981 [GB] United Kingdom ............... 8122989

[51] Int. Cl.³ ............................................. G01N 29/04
[52] U.S. Cl. ....................................... 73/644; 128/661
[58] Field of Search ............... 73/644; 252/316, 408.1; 128/661, 663

[56] References Cited

U.S. PATENT DOCUMENTS

| | | | |
|---|---|---|---|
| 3,661,146 | 5/1972 | Peronneau | 73/644 |
| 3,826,127 | 7/1974 | Molina | 73/644 |
| 4,002,221 | 1/1977 | Buchalter | 73/644 |
| 4,269,068 | 5/1981 | Molina | 73/644 |
| 4,333,352 | 6/1982 | Connery et al. | 73/644 |
| 4,365,516 | 12/1982 | Molina | 73/644 |

Primary Examiner—James J. Gill
Attorney, Agent, or Firm—Cushman, Darby & Cushman

[57] ABSTRACT

An ultrasonic transducer is improved, particularly for use in perivascular blood flow measurement, by the provision of a coupling member made of a hydrogel. The hydrogel is suitably acrylic based; has a water content in the range from 75 to 90% by weight and preferably about 85%; and has acoustic attenuation of less than 2 dBcm$^{-1}$ at 5 MHz, with longitudinal velocity of sound and acoustic impedance of similar order to those for tissue. The crystals of the transducer are preferably sealed from the coupling member by a water resistant coating, the member suitably has an exposed face of part cylindrical shape to accommodate a vascular vessel, and the member is preferably releasably mounted to allow size interchange for different vessels.

10 Claims, 1 Drawing Figure

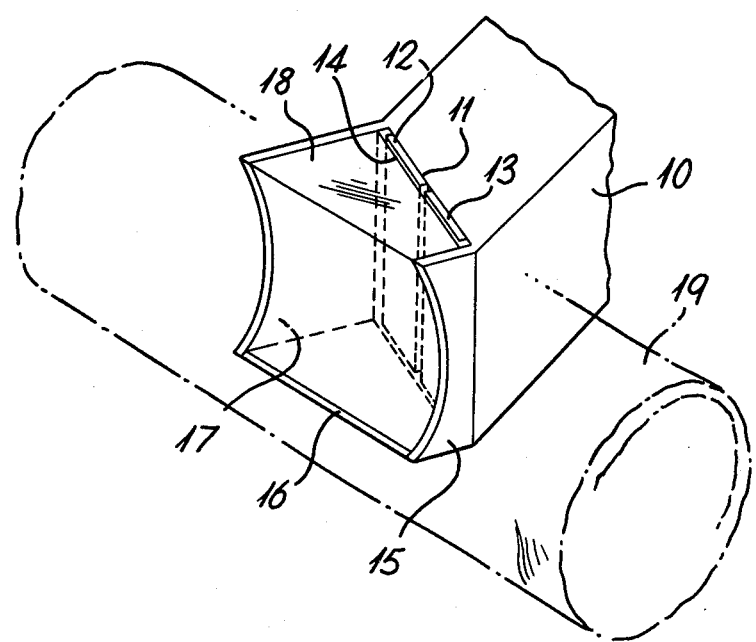

ULTRASONIC TRANSDUCER COUPLING MEMBER

This invention concerns ultrasonic transducers and more particularly, but not exclusively, such transducers for use in perivascular blood flow measurement in association with vascular surgery.

Measurements of blood flow in the major vessels of the body have been made with both electromagnetic and ultrasonic flowmeters. Use of the former has been largely restricted to exposed vessels but, although the instrumentation has been developed to a high degree, there is a considerable potential for significant errors in the resultant measurements. These errors are mainly associated with the unknown electrical properties of the relevant vessels and errors of up to 50% are possible. Ultrasonic blood flowmeters, in contrast, are less problematical in use and are normally employed transcutaneously, this last feature being clearly preferable for the primary interest in blood flow measurements, namely, diagnosis of vascular conditions.

In these circumstances electromagnetic blood flowmeters have fallen largely into disuse, and ultrasonic forms are now employed on an increasing scale.

However a need remains for the perivascular measurement of blood flow in association with vascular surgery. Such measurement can reveal small technical imperfections at the time of surgery which lead to failure if not corrected, it can demonstrate that a sufficient volume flow exists for the purpose of tissue perfusion, and it can demonstrate that the mean flow velocity is sufficient to avoid re-thrombosis in the first months following surgery.

While existing ultrasonic blood flowmeters may appear as well suited to perivascular use as transcutaneous use, this is not in fact the case. A particular difficulty arises in connection with coupling of an ultrasound transducer with a vascular vessel. Ultrasound/tissue coupling conventionally involves a water bath, which is clearly inappropriate in the present context, or a water-soluble gel, which is also inappropriate in a wet surgical field.

An object of the present invention is to obviate the difficulties of this last situation and, to this end, it is proposed that the transducer with a coupling member made of a synthetic polymer of a kind termed a hydrophylic gel and commonly referred to as a hydrogel.

A coupling member of hydrogel can provide several benefits relevant to this proposed use.

One benefit resides in acoustic properties. A hydrogel can effect low acoustic attenuation, typically less than $2 dBcm^{-1}$ at a signal frequency of 5MHz. Also, the longitudinal velocity of sound in a hydrogel can be fairly close to $1500 ms^{-1}$, thus avoiding large refractions at the interface with a vascular vessel. In addition, the characteristic acoustic impedance can be closely matched to that of tissue, i.e. $1.5 \times 10^{-6} kg\ m^{-2}s^{-1}$.

A factor relevant to this benefit is that a hydrogel can have a major water content which, for the present purpose, is suitably between 75 and 90% by weight, and preferably about 85%.

Another benefit is that a hydrogel can, notwithstanding a water content such as just mentioned, have adequate mechanical stability for use in a wet field.

Further benefits include the fact that hydrogels are capable of, and indeed are noted in their use for contact lenses for, biological inertness by an absence of mechanical and chemical irritation, and they can withstand sterilisation procedures appropriate for surgical instrumentation.

It will be understood that one hydrogel does not necessarily provide an ideal balance of these benefits, but satisfactory results can be obtained with hydrogels among those currently available and improved results are possible with further development. The satisfactory results in question have involved acrylic based hydrogels, and the favoured one at present is a copolymer of vinyl pyrrolidone and phenethyl methacrylate.

It is also preferred in practice that the crystal component of the transducer be provided with a water resistant coating to protect the same from water in the hydrogel and the liquid environment when in use. A polyester resin has been found suitable for this coating, but the choice of substance is not critical providing that it prevents water absorption and does not markedly absorb ultrasound, or otherwise significantly distort the acoustic transmission.

For perivascular use, the coupling member will suitably have an exposed face concavely profiled to a part-circular-cylindrical shape to complement the shape of a vascular vessel. Also, because the diametral size of vessels varies, over a range of about 3-25 mm, the selective use of coupling members having differently sized profiles is appropriate. Accordingly, the transducer is preferably such as to secure an associated coupling member in releasable manner whereby to allow interchangeable connection with different ones of a range of members having varying profiled portions but commonly formed transducer-engaging portions. This feature is also appropriate to the use of disposable coupling members, suitably made available individually in pre-sterilised packs.

The accompanying drawing schematically illustrates a transducer according to the present invention.

The illustrated transducer has a main body 10 of elongated probe form terminating at one end in a transversely inclined face 11 on which are mounted, in side-by-side disposition, transmitting and receiving crystals 12 and 13. These crystals are, as proposed above, suitably covered with a water resistant coating 14.

The transducer body is extended from the periphery of its face 11 by three walls 15, 16 and 17 forming a housing for a coupling member 18 of hydrogel. The opposed walls 15 and 17 are interconnected by the wall 16, and are each similarly concavely profiled along their outermost edges, but are of differing heights so that the housing defines a generally trapezoidal space. The member 18 is of shape complementary to this space to allow insertion and separation by sliding through the open side of the housing, but the member may have differing concavity over its outer face to facilitate engagement over a given vascular vessel (denoted at 19 in broken outline) as mentioned above.

The overall geometrical configuration of this transducer is useful in facilitating visual guidance to locate the coupling member on to a vessel, but other configurations are possible. Similarly, the coupling member housing is but one example of an arrangement allowing interchangeability between coupling members.

We claim:

1. An ultrasonic transducer comprising a coupling member made of a hydrogel which is mechanically stable in a wet surgical field.

2. A transducer according to claim 1 wherein said hydrogel has a water content in the range from 75 to 90% by weight.

3. A transducer according to claim 2 wherein said water content is about 85% by weight.

4. A transducer according to claim 2 wherein said hydrogel has at least one of the following properties: acoustic attenuation of less than $2 dBcm^{-1}$ at a frequency of 5MHz, longitudinal velocity of sound of approximately $1500 ms^{-1}$, and acoustic impedance of about $1.5 \times 10^{-6} kg\, m^{-2} s^{-1}$.

5. A transducer according to claim 2 wherein said hydrogel is of acrylic based form.

6. A transducer according to claim 5 wherein said hydrogel is a copolymer of vinyl pyrrolidone and phenethyl methacrylate.

7. A transducer according to claim 1 having adjacent said coupling member a crystal component which has a water resistant coating.

8. A transducer according to claim 7 wherein said coating is of a polyester resin.

9. A transducer according to claim 1 wherein said coupling has an exposed face concavely profiled to a substantially part cylindrical shape.

10. A transducer according to claim 1 wherein said coupling is releasably mounted therewith.

* * * * *